United States Patent [19]

Herrell

[11] Patent Number: 4,695,254
[45] Date of Patent: Sep. 22, 1987

[54] TOOTH REPLACEMENT

[76] Inventor: John M. Herrell, 106 Hazard Rd., Carpentersville, Ill. 60110

[21] Appl. No.: 790,868

[22] Filed: Oct. 24, 1985

[51] Int. Cl.[4] ............................................. A61C 11/00
[52] U.S. Cl. ...................................... 433/213; 433/40; 249/54
[58] Field of Search .................... 433/40, 34, 36, 202, 433/213, 175, 215, 159, 160, 223; 249/160, 54, 161, 162, 163; 264/16, 19

[56] References Cited

U.S. PATENT DOCUMENTS

| | | | |
|---|---|---|---|
| 512,840 | 1/1894 | Phelps | 249/161 |
| 833,883 | 10/1906 | Lentz | 433/213 |
| 1,024,152 | 12/1913 | Smith | 264/16 |
| 1,465,472 | 8/1923 | Hansen | 433/223 |
| 1,654,026 | 12/1927 | Veatch | 249/160 |
| 3,057,069 | 10/1962 | Clemente | 433/223 |
| 3,343,263 | 9/1967 | Henlotter | 433/175 |
| 3,919,773 | 11/1975 | Freeman | 433/175 |
| 4,097,992 | 7/1978 | Hazar | 433/171 |
| 4,162,625 | 7/1979 | Simmons | 433/34 |
| 4,199,864 | 4/1980 | Ashman | 433/223 |
| 4,244,689 | 1/1981 | Ashman | 433/175 |
| 4,457,714 | 7/1984 | Klein | 433/213 |
| 4,468,202 | 8/1984 | Cohen | 433/214 |

FOREIGN PATENT DOCUMENTS 0514830 11/1939 United Kingdom ............... 264/16

Primary Examiner—Gene Mancene
Assistant Examiner—Adriene J. Lepiane
Attorney, Agent, or Firm—Mathew R. P. Perrone, Jr.

[57] ABSTRACT

A tooth replacement is formed by reconstructing a defective tooth in place in the mouth; extracting the reconstructed tooth; forming a die to shape an artificial tooth using the extracted tooth as a model; making a mold from the die; filling the mold with a pharmaceutically-acceptable resin; curing or hardening the resin; extracting the thus-formed tooth from the mold; and inserting the artificial tooth thus formed into the place formerly occupied by the extracted tooth to permit the jaw to grow around and seat the root of the artificial tooth.

17 Claims, 12 Drawing Figures

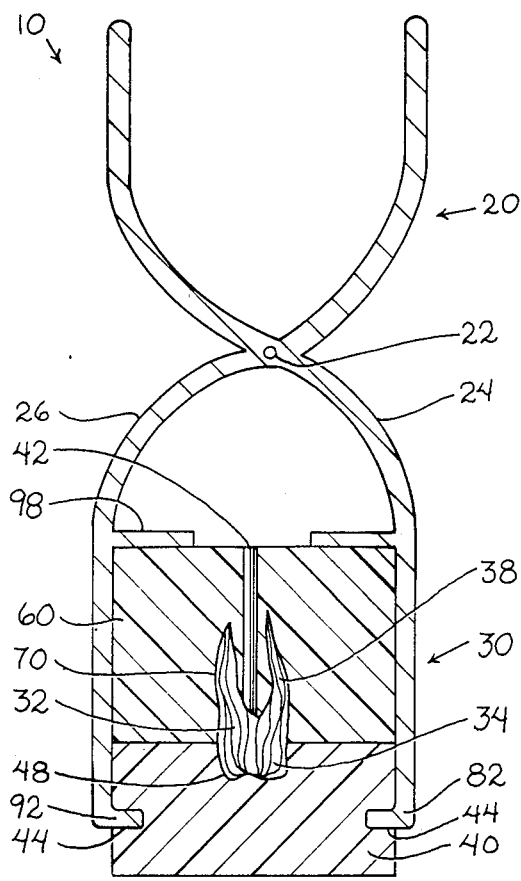
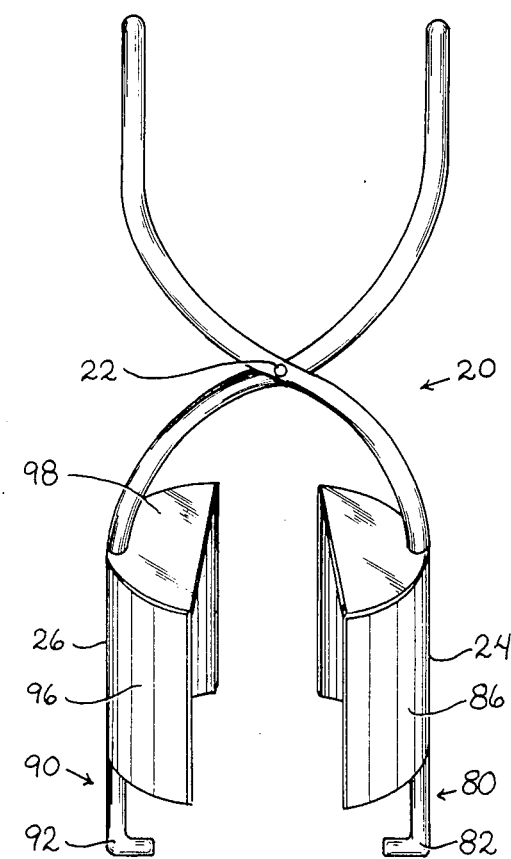
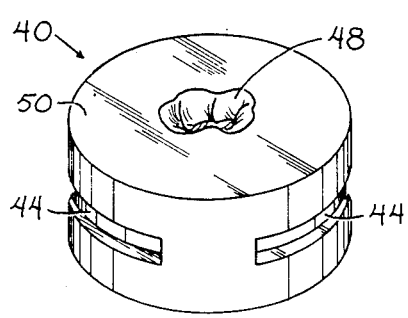
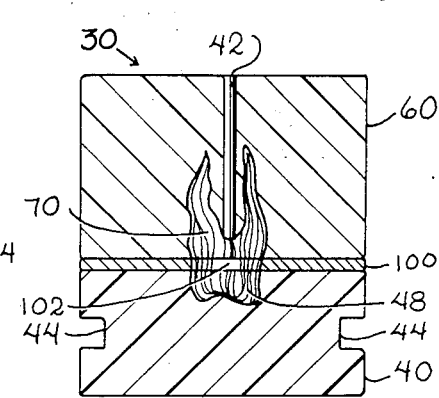
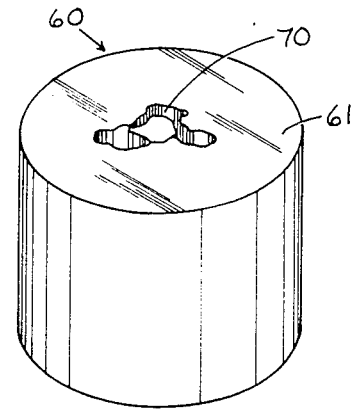
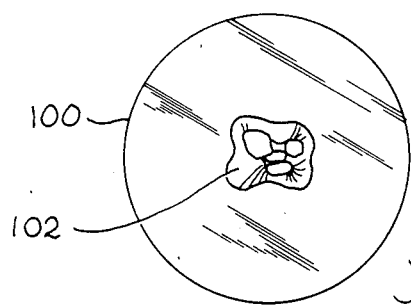
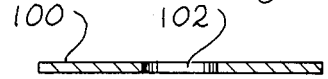

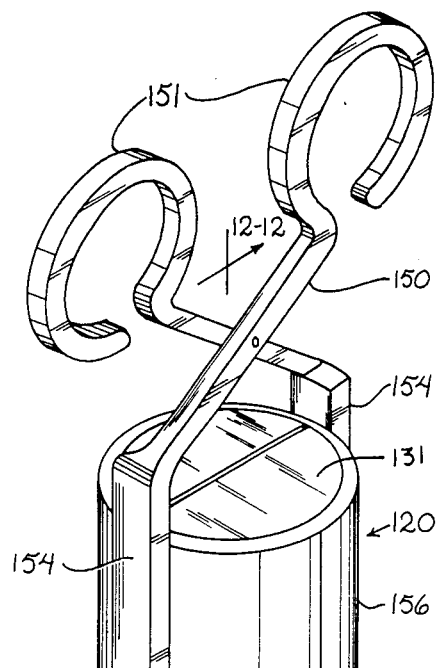
Fig. VIII
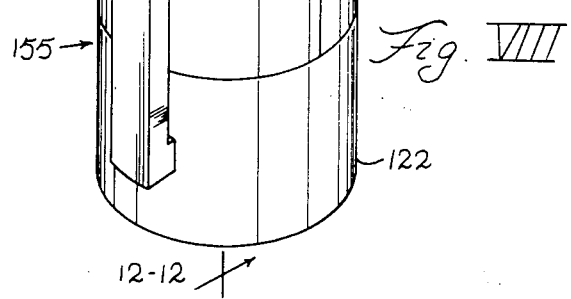
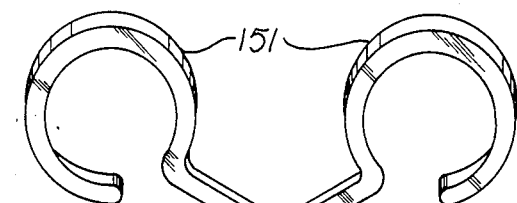
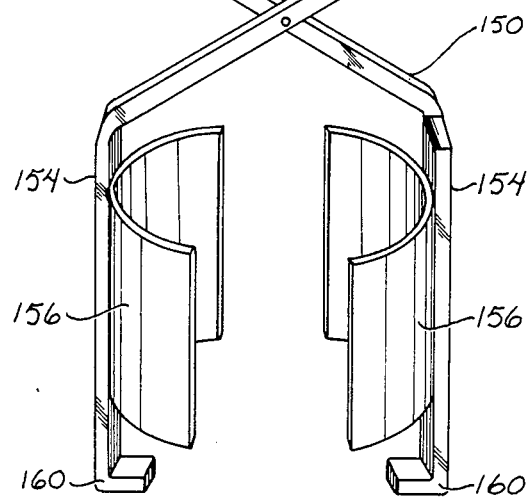
Fig. XI
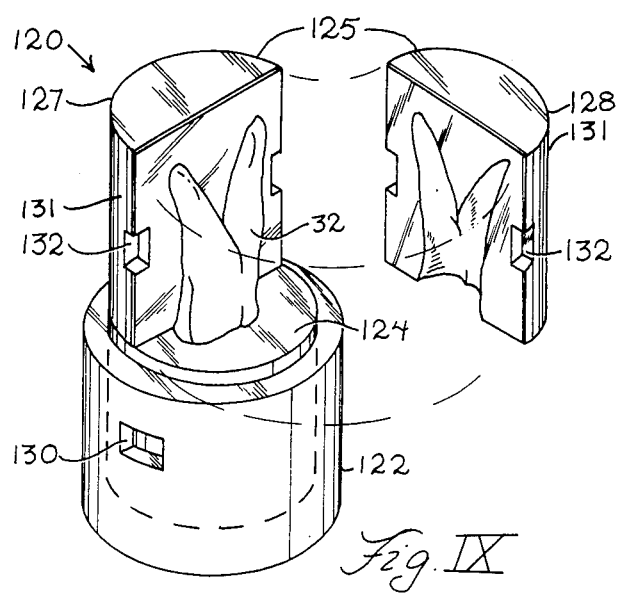
Fig. IX
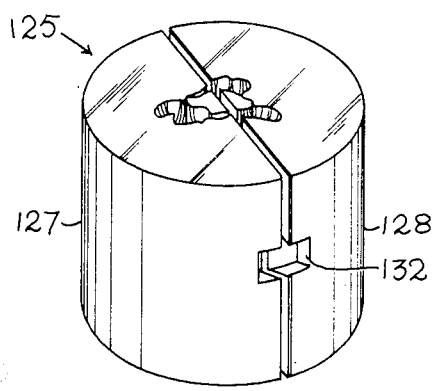
Fig. X
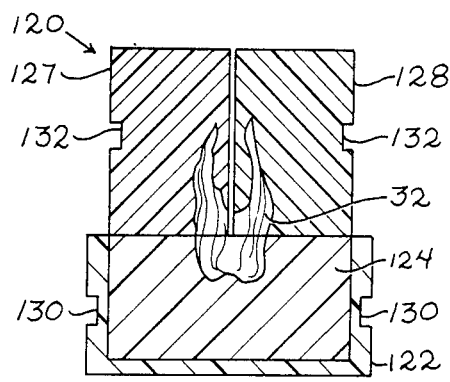
Fig. XII

4,695,254

TOOTH REPLACEMENT

BACKGROUND OF THE INVENTION

This invention relates to a tooth replacement and more particularly to a method and apparatus for making a tooth and inserting the tooth into the mouth where the tooth is a substantially exact duplicate of the tooth it replaces.

All animals suffer from tooth decay or problems with teeth. Whether the animal is a domestic or wild animal, or human animal; tooth problems exist. From the human side of tooth problems, research indicates that even the caveman did not escape tooth problems. As is well-known, tooth problems continue to this day.

Standard dentistry procedures for correcting tooth problems are very well known. Decay can be drilled away and replaced, so that the tooth is filled to substantially its original by suitable materials. It is also feasible to replace entire groups of teeth with denture plates. These standard dentistry procedures have their limitations.

A tooth can be filled only so often without being destroyed. If the tooth breaks beyond filling, a customary procedure is to put in a crown using the natural root of the tooth already implanted as a base for that crown. However, even crowns do not always work, because a sufficient amount of tooth may not remain to secure a crown in place. If the crown does not work, a complete or partial bridge is necessary. Such procedures are complicated and expensive.

Yet, the full number of teeth in the mouth is desirable for aesthetic reasons and health reasons as well. Gaps in the mouth, where an extracted tooth or teeth use to be, are customarily filled by the other teeth moving out of position into those gaps. Such tooth movement causes a great number of problems. The movement of the other teeth into the gap caused by the pulled tooth can affect the bite and cause other physical problems, as well as adversely affect the aesthetic appearance of the person.

Mounting of caps or bridges to solve these aesthetic or physical problems—whether partial bridges or full bridges—becomes very difficult. The mounting must be secured in the mouth in some fashion. No artificial mounting replaces the mounting of the regular jaw. The support of the tooth in the regular jaw support is clearly the best method of mounting the teeth in jaw.

Attempts to solve these problems by implanting artificial teeth must overcome major problems. One of the major problems of implanting artificial teeth in the body is to overcome phenomenon of rejection. This phenomenon is a natural defense of the body. The human body utilizies two major lines of defense. If elements in the body encounter a foreign object, elements in the body try to destroy that object. For example, when white cells encounter bacteria in the blood, the white cells try to devour the bacteria. If that fails, the body tries to eject that material from the body. So whenever foreign objects are planted in the body, the body must be convinced that this is an acceptable addition to the body. This occurs with regard to artificial valves for the heart or pacemakers, or any other artificial substance that is implanted in the body.

It thus becomes clear that it is highly desirable to avoid gaps left by pulled teeth while at the same time providing for a desirable method of replacing the gaps.

SUMMARY OF THE INVENTION

Therefore, it is an object of this invention to provide a method for replacing an extracted tooth.

A further object of this invention is to provide a method of molding a suitable artificial tooth.

A still further object of this invention is to provide a method for mounting an artificial tooth in the mouth.

Yet a further object of this invention is to provide a method for making an artificial tooth.

Also an object of this invention is to provide an apparatus for molding an artificial tooth.

Another object of this invention is to provide an apparatus for clamping the mold of an artificial tooth.

Yet another object of this invention is to provide a replacement for a crown.

Still another object of this invention is to provide a replacement for a bridge.

A further object of this invention is to provide a method for avoiding the shifting of teeth in the mouth.

Still, a further object of this invention is to provide a method for avoiding gaps caused by a pulled tooth in the mouth.

Yet a further object of this invention is to provide an artificial tooth which is accepted by the body.

Also an object of this invention is to provide an artificial tooth which avoids rejection by the body.

These and other objects of the invention are met by reconstructing a defective tooth in place in the mouth; extracting the reconstructed tooth; forming a die to shape an artificial tooth using the extracted tooth as a model; making a mold from the die; filling the mold with a pharmaceutically-acceptable resin; curing or hardening the resin; extracting the thus-formed tooth from the mold; and inserting the artificial tooth thus formed into the place formerly occupied by the pulled tooth to permit the jaw to grow around the root of the artificial tooth and seat it. The mold is two, three, or more parts and usually cylindrical in shape and is clamped together by a mold clamp of the pliars type.

BRIEF DESCRIPTION OF THE DRAWINGS

FIG. I is a cross-sectional view of the mold assembly 10 of the invention.

FIG. II is a partial perspective view of the mold clamp 20.

FIG. III is a perspective view of the mold top 40.

FIG. IV is a cross-sectional view of FIG. I with clamp 20 removed—showing spacer 100.

FIG. V is a perspective view of mold base 60.

FIG. VI is a top view of spacer 100.

FIG. VII is a cross-sectional view of spacer 100.

FIG. VIII is a perspective view of three part mold 120 having tri-mold clamp 150 secured thereto FIG. IX is an exploded view of three part mold 120 with tri-mold clamp 150 removed.

FIG. X is a perspective view of trimold top 125.

FIG. XI is a perspective view of trimold clamp 150.

FIG. XII is a cross-sectional view of three part mold 120 along Line 12—12 of FIG. VIII.

Throughout the figures of the drawing where the same part appears in more than one figure of the drawing, the same number is applied thereto.

DESCRIPTION OF THE PREFERRED EMBODIMENTS

Tooth implants are achieved by reconstructing the tooth in place, extracting the tooth, forming an artificial tooth using the extracted tooth as a model, and inserting the artificial tooth in the appropriate place (that is the spot from which the extracted tooth is pulled) in the mouth.

Basically, with a damaged tooth, repairs must be made to reconstruct a tooth as nearly as possible to its original condition with special attention being paid to the original shape of the tooth. This can be done by standard filling procedures, resin bonding, a crown or another suitable fashion. Expensive material does not have to be used in this fashion. It is only desired to provide the appropriate shape of the tooth, and have the tooth be durable enough to form a mold. The tooth as repaired can be then be extracted.

After a tooth as repaired is extracted and cleaned, it is inserted between two sections of shapeable material. The two sections are then clamped together with the tooth in the material and held there until the mold hardens. At that point, the reconstructed tooth can be removed from the mold, and the mold can be filled with an artificial material—such as surgically acceptable acrylic resin—to form an artificial tooth. This surgically acceptable acrylic resin is then hardened. The hardened artificial tooth is then extracted from the mold and placed in the socket.

Before pulling the tooth, the dentist must repair the tooth so it is in adequate shape. The dentist must then measure and determine the appropriate mold surface for fitting the tooth head. The gum must be numbed and given an injection to reduce the swelling. After the medicine has worked, the dentist must then pull the tooth. After appropriate cleaning, the tooth is inserted into the mold. The mold is clamped into position with the mold clamp and dipped into a sealant. This plastic sealant produces the hard tooth. The form is dipped into cold water to harden the plastic. Then the original tooth is removed from the mold.

The mold is in two pieces having a root piece and a cap piece. The mold roots are filled with acrylic resin or other pharmaceutically acceptable resin that can be light hardened or catalytically hardened sufficient to replace a tooth. The resin passes through the root section into the crown section.

The tooth cavity is then cleaned or may be cleaned after the extraction. The artificial tooth may then be inserted into the tooth cavity. At that time, it is possible to apply a brace to hold the tooth in place until the gums and jaw bone have accepted the tooth to make for an accepted artifical tooth. This process clearly reduces the need for jaw bone implants and dentures. In this fashion, by placing the tooth back in place, the deterioration of the jaw bone is avoided.

Referring now to FIG. I, the mold assembly 10 includes mold clamp 20 and mold form 30. Mold form 30 has a mold top 40 which receives tooth 32 at the crown 34 of the tooth 32 and mold base 60 which receives the roots 38 of the tooth 32 and mold base 60 which receives the roots 38 of the tooth 32. Mold form 30 is made of hardenable plastic that can be impressioned by the extracted tooth 32.

Additionally, the hardened plastic of mold base 60 can have an aperture 42 formed therein for inserting the acrylic resin or other suitable resin to form the artificial tooth. Normally, this aperture for inserting the resin is formed in the mold base 60 or root section of the mold form 30. Both the mold base 60 and the mold top 40 are cylindrical in shape.

Mold top 40 has therein clamp receiving slots 44 oppositely disposed from each other. The clamp receiving slots 44 position mold clamp 20 on the mold and hold the mold in position until the tooth material is cured.

Mold clamp 20 is basically a pliars-type, scissors, first-class lever arrangement having a pivot rod 22 centrally located between and movably securing first jaw 24 to second jaw 26. Both first jaw 24 and second jaw 26 are substantially mirror images of each other.

The cross-section of the mold assembly 10 shows the positioning of the tooth 32 in mold assembly 10 with clamp 20 being in position. First base flange 86 and second base flange 96 are shown as having a shelf 98 for the purpose of holding mold base 60 to mold top 40. The shelf grips the mold base while the first jaw end 82 and second jaw end 92 fit in clamp receiving slots 44 and hold the mold together.

Referring now to FIG. II, first jaw 24 has a first jaw end 80. First jaw end 80 includes first mold top holder 82 designed to fit into one of clamp receiving slots 44. Adjacent the mold top holder 82 and between pivot rod 22 of the holder 20 is first base flange 86 to hold the base 60 adjacent to the mold top 40. In this fashion, the mold 20 can be locked together to from a mold form the extracted tooth or to shape the artificial tooth.

Second jaw 26 has a second jaw end 90. Second jaw end 90 includes second mold top holder 92 designed to fit into one of clamp receiving slots 44. Adjacent second mold top holder 92 and between pivot rod 22 of the holder 20 is second base flange 96 to hold the base 60 adjacent to the mold top 40. In this fashion, the mold 20 can be locked together to form a mold around the extracted tooth, which mold can, in turn, be used to shape the artificial tooth.

Referring now to FIG. III, a perspective view of mold top 40 is observed. A perspective view of mold top 40 is shown showing crown receiver 48 centrally located in the bottom 50 of mold top 40. Clamp receiving slots 44 serve to receive first jaw end 82 and second jaw end 92 and hold the mold top 40 in conjunction with the mold base 60.

Referring now to FIG. IV, mold 30 is shown with spacer 100 between mold top 40 and mold base 60. Spacer 100 serves to permit more thorough clamping of the mold 30 in order to form the tooth in a more sophisticated fashion. FIG. IV, being a version of FIG. I with clamp 20 removed, gives a clear idea of the function of the mold without the clamp.

A perspective view of mold base 60 is seen in FIG. V. Spacer side 61 of mold base 60 shows root receiver 70 in perspective. Root receiver 70 is used to form the shaping surface for the roots of a tooth and to shape the roots of the artificial tooth. Mold base 60 cooperates with mold top 40 to shape the whole artificial tooth.

FIG. VI and FIG. VII combine to show the spacer availability. FIG. VI is a top view of the spacer 100. FIG. VII is a cross-section view of the spacer 100. Centrally located in spacer 100 is a spacer aperture 102 which corresponds to the root receiver 70 in base 60 and a crown receiver 48 in mold top 40. In this fashion, the mold can be locked together and secured so that the tooth can be properly formed.

FIG. VIII depicts tri-part mold 120 with tri-mold clamp 150 in position. Tri-part mold 120 is similar to mold 30 but for the fact that the mold is in three pieces as opposed to two. Tri-part mold 120 includes a mold cup 122. Mold cup 122 receives mold material 124 therein.

Referring now to FIG. IX, FIG. X and FIG. XII, mold material 124 is shaped by the reconstructed tooth. Mold material 124 in base cup 122 receives the crown of the tooth. Tri-part root section 125 includes two parts to form the root section of the tooth. A left hand part 127 and a right hand part 128 consists of the same mold material 124 to shape the crown of the tooth. However, left hand part 127 and right hand part 128 separate upon release of tri-mold clamp 150 to permit the tooth to be easily removed therefrom. Root section 125 includes a cover for holding mold material 124 in root section 125. Cover 131 holds the mold material and is split in two halves for receiving mold material 124 to simplify removal of the tooth from the root section 125. Cup 122 includes tri-mold clamp receivers 130 for the purpose of positioning tri-mold clamp 150 on the cup 122 and root section 125. In a similar fashion, root tri-mold clamp receivers 132 provide for holding means for the tri-mold clamp 150 on the mold. Tri-mold clamp 150 is shaped suitable to correspond to the mold.

Referring now to FIG. VIII and FIG. XI, tri-mold clamp 150 is a typical scissors type apparatus having scissor-type handles 151. Clamp jaws 154 are positioned along mold sides 155 to hold mold shapers 156 in position on the mold. Clearly the mold shapers 156 are positioned to receive the root section 125, while the tri-mold clamp 150 has mold grabbers 160 at the tips thereof to fit into crown receivers 130 and a corresponding pair of root receivers 132 in root section 125. This three part mold provides for simpler removal of the material from the mold. After the artifical tooth is properly formed, it can then be inserted in the jaw.

Thus, it may be seen that it is feasible to form an artificial tooth having the same hardness as the natural. In this fashion, the artificial tooth may be held in place in the jaw. This eliminates the need for an additional artificial structure in the mouth. The jaw and other functions which supported the natural tooth now support the artificial tooth because of its similar shape to the natural tooth and the acceptability of the tooth material to the human body.

Because of the disclosure herein and solely because of the disclosure herein, certain modifications of the device disclosed and claimed herein can become apparent to those having ordinary skill in this art. Such modifications are clearly covered hereby.

What is claimed and sought to be secured by Letters Patent of the United States is:

1. A method for providing an artificial, replacement tooth for to avoid gaps caused by a pulled tooth in a mouth; wherein said artificial tooth has at least one root and a crown and wherein said method comprises:
   a. reconstructing a defective tooth in place in said mouth to form a reconstructed tooth, having at least one natural root and a reconstructed portion;
   b. extracting said reconstructed tooth having said at least one natural root and said reconstructed portion to form a empty socket in said mouth;
   c. forming a die to shape an artificial tooth using said extracted, reconstructed tooth as a model;
   d. making a mold from the die;
   e. filling said mold with a pharmaceutically acceptable resin;
   f. hardening said pharmaceutically acceptable resin to form an artificial tooth having said at least one root and said crown as a substantial duplicate of said reconstructed tooth;
   g. removing said artificial tooth from said mold; and
   h. inserting said artificial tooth into said socket to permit a jaw to grow around said at least one root of said artificial tooth and seat said artificial tooth in said jaw.

2. The method of claim 1 wherein:
   a. said mold has a root section and a crown section made of shapeable material;
   b. said root section and said crown section are clamped together with said reconstructed tooth in said shapeable material; and
   c. said shapeable material is hardened.

3. A mold assembly for forming an artificial tooth having roots and a crown wherein:
   a. said mold assembly includes a mold form and a removable clamping means for holding said mold form together;
   b. said mold form includes a root piece and a cap piece;
   c. said root piece and said cap piece are secured together by said clamping means;
   d. said root piece forms a root of said artificial tooth and said cap piece forms a crown of said artificial tooth;
   e. said clamping means removably secures said root piece and said cap piece together;
   f. a flexible spacer is inserted between said cap piece and said root piece; and
   g. said clamping means compresses said flexible spacer to hold said mold tightly.

4. The mold assembly of claim 3 wherein said mold form is made of hardenable material, said hardenable material being capable of receiving an impression of said extracted tooth in a softened state and then being hardened to form a mold.

5. The mold assembly of claim 4 wherein said root piece includes an aperture for infusing a pharmaceutically acceptable resin into said mold form to form said artificial tooth.

6. The mold assembly of claim 5 wherein said mold form is cylindrical in shape.

7. The mold assembly of claim 6 wherein:
   a. said cap piece is cylindrical in shape; and
   b. said cap piece has a pair of oppositely-disposed, clamp receiving slots in a cylindrical wall therein.

8. The mold assembly of claim 7 wherein:
   a. said clamping means is a mold clamp;
   b. said mold clamp includes a pliers-type, scissors, first-class lever arrangement having a first jaw and a second jaw oppositely disposed from said second jaw;
   c. a pivot rod acts as a fulcrum and movably secures said first jaw to said second jaw; and
   d. said first jaw is substantially a mirror image of said second jaw.

9. The mold assembly of claim 8 wherein:
   a. said mold clamp includes a handle end and a jaw section oppositely disposed from said handle end;
   b. said pivot rod is situated between said handle end and said jaw section;
   c. said jaw section includes said first jaw and said second jaw;
   d. a first base flange is secured to said first jaw;
   e. a second base flange is secured to said second jaw; and f. said first base flange and said second base flange are hemi-cylindrical in shape.

10. The mold assembly of claim 9 wherein:
a. said first base flange and said second base flange are hemi-cylindrical in shape;
b. a first shelf is a top part of said first base flange for a purpose of holding said root piece to said cap piece;
c. a second shelf is a top part of said second base flange for a purpose of holding said root piece to said cap piece;
d. a first jaw end is oppositely disposed from said first shelf and capable of fitting into one of said clamp receiving slots;
e. a second jaw end is oppositely disposed from said second shelf and capable of fitting into one of said clamp receiving slots; and
f. said first jaw end and said first shelf cooperate with said second jaw end and said second shelf to hold said cap piece and said root piece together for molding said artificial tooth.

11. A tri-part mold assembly for forming an artificial tooth having roots and a crown wherein:
a. said mold assembly includes a tri-part mold form and a removable tri-mold clamping means for holding said tri-part form together;
b. said tri-part form includes a root section and a crown section;
c. said root section and said crown section are secured together by said clamping means;
d. said root section forms said roots of said artificial tooth and said crown section forms a crown of said artificial tooth;
e. said clamping means removably secures said root section and said crown section together;
f. a flexible spacer is inserted between said cap piece and said root piece; and
g. said clamping means compresses said flexible spacer to hold said mold tightly.

12. The tri-part mold assembly of claim 11 wherein said tri-part mold form is made of hardenable material, said hardenable material being capable of receiving an impression of said extracted tooth in a softened state and then being hardened to form a tri-part mold.

13. The tri-part mold assembly of claim 12 wherein said root section includes an aperture for infusing a pharmaceutically acceptable resin into said tri-part mold form to form said artificial tooth.

14. The tri-part mold assembly of claim 13 wherein:
a. a flexible spacer is inserted between said crown section and said root section; and
b. said clamp compresses said flexible spacer to hold said tri-part mold tightly.

15. The tri-part mold assembly of claim 14 wherein:
a. said tri-part mold assembly includes a mold cup for holding an impressionable molding material;
b. said mold cup includes a root section and a crown section;
c. said root section includes a left section and a right section;
d. said crown section, said left section and said right section are held together by said clamping means; and
e. said left section and said right section separate to permit simplified removal of the tooth form the mold.

16. The tri-part mold assembly of claim 15 wherein:
a. said tri-part clamping means is shaped to receive said tri-part mold;
b. said tri-part clamping means has scissors-type handles, and a pair of tri-part mold shapers positioned to receive said root section and a pair of tri-part mold grabbers oppositely disposed from said handles; and
c. said tri-part mold grabbers fit into a pair of crown receivers on said crown section.

17. The tri-part mold assembly of claim 16 wherein said tri-part mold form is cylindrical in shape.

* * * * *